United States Patent [19]

Lindegren et al.

[11] Patent Number: 5,445,859
[45] Date of Patent: Aug. 29, 1995

[54] MULTIPOLAR ELECTRODE LEAD

[75] Inventors: Ulf Lindegren, Enskede, Sweden; Helmut Freller, Roethenbach; Peter Lorenz, Schwarzenbruck, both of Germany

[73] Assignee: Siemens Aktiengesellschaft, Munich, Germany

[21] Appl. No.: 105,158

[22] Filed: Aug. 12, 1993

[30] Foreign Application Priority Data

Aug. 14, 1992 [SE] Sweden .................................. 9202351
Sep. 30, 1992 [SE] Sweden .................................. 9202824

[51] Int. Cl.$^6$ .............................................. B32B 9/00
[52] U.S. Cl. ................................... 428/76; 29/605; 29/618; 428/901; 428/70; 128/639
[58] Field of Search ............... 128/418, 784, 785, 783; 29/605, 618; 428/76, 901, 70

[56] References Cited

U.S. PATENT DOCUMENTS

| | | | |
|---|---|---|---|
| 3,348,548 | 10/1967 | Chardack | 128/418 |
| 4,437,474 | 3/1984 | Peers-Trevarton | 128/784 |
| 4,662,382 | 5/1987 | Sluetz et al. | 128/785 |
| 4,788,329 | 11/1984 | Friedman | 128/418 |
| 4,947,866 | 8/1990 | Lessar et al. | 128/784 |

FOREIGN PATENT DOCUMENTS

| | | |
|---|---|---|
| 536183 | 4/1984 | Australia . |
| 0092797 | 11/1983 | European Pat. Off. . |
| 656313 | 6/1986 | Switzerland . |

OTHER PUBLICATIONS

Advertisement of Diamonex, Incorporated for Diamonex Products.
"Plasma Assisted CVD For Biomedical Applications", Grant et al, Diamond And Related Materials, vol. 1 (1992), pp. 727–730.

Primary Examiner—Patrick J. Ryan
Assistant Examiner—Kam F. Lee
Attorney, Agent, or Firm—Hill, Steadman & Simpson

[57] ABSTRACT

A multipolar electrode lead, of the type used to deliver electrical energy in vivo to tissue as part of a system for medical electrotherapy, contains at least first and second conductors, with at least the first conductor being provided with an insulating coating which electrically separates the conductors from each other. The risk of the insulating coating being worn off and a short-circuit developing are reduced by forming the insulating coating of a material having a high electrical resistance and a resistance to abrasion.

18 Claims, 2 Drawing Sheets

MULTIPOLAR ELECTRODE LEAD

BACKGROUND OF THE INVENTION

1. Field of the Invention

The present invention relates to a multipolar electrode lead of the type used with a medical apparatus for delivering electrotherapy, such as electrical stimulation pulses, in vivo to living tissue.

2. Description of the Prior Art

Medical electrode leads are generally known in the art which include an insulating sheath containing a coiled first conductor and a coiled second conductor which are coaxially arranged, with at least the first conductor being covered by an insulating coating so as to electrically separate the conductors from each other.

One such known electrode lead is disclosed in German OS 3 031 752. This known electrode lead contains a plurality of electrode conductors, each of which is provided with an insulating coating consisting of a polymer or the like to electrically separate the respective conductors. The insulated conductors are in the form of respective coiled conductors, disposed next to each other within the insulating sheath at the same distance from the center axis of the electrode lead.

After implantation in the vascular system of a patient, an electrode lead is flexed back and forth by movements of the body of the patient and blood vessels. The insulating polymer coating in the aforementioned known electrode lead could then rub off between two conductors, leading to a short-circuit.

SUMMARY OF THE INVENTION

It is an object of the present invention to provide an electrode lead of the type described above which is capable of withstanding high mechanical stress without a short-circuit developing between two conductors.

The above object is achieved in accordance with the principles of the present invention an electrode lead of the type having an insulating sheath with at least two coiled conductors therein, wherein at least one of the conductors is coated with a material having a high electrical resistance and which is abrasion-resistant.

The high-resistance, abrasion-resistant coating insulates the conductors from each other while reducing the risk of short-circuiting. Because the high-resistance, abrasion-resistance coating can be made thinner than a conventional polymer insulating coating (which must be thicker than is electrically warranted in order to reduce the risk of wearing away due to mechanical stress) the entire electrode lead can be made thinner.

In an embodiment of the invention, the second conductor is a separate conductor wire provided with a thin coating of material which is abrasion-resistant and which has a high electrical resistance.

In this embodiment, since both conductors are provided with a high-resistance, abrasion-resistant coating, the electrical insulation between the conductors is further enhanced.

A suitable material for the high-resistance, abrasion-resistant coating is preferably DLC (diamond-like carbon, also known as amorphous diamond). If this material is used as the high-resistance, abrasion-resistant coating, it is preferably applied to the relevant conductor in a thickness in the range from 0.1 to 10 $\mu$m, preferably in the range between 1 and 5 $\mu$m.

In a further embodiment, the high-resistance, abrasion-resistant coating may be formed by a first layer consisting of a highly electrically resistant material and a second layer consisting of an abrasion-resistant material.

As a result of the presence of the abrasion-resistant layer in this embodiment, the layer consisting of highly electrically resistant material is not exposed to significant abrasion stress when the electrode lead flexes, and is protected by the abrasion-resistant coating. Therefore, the high-resistance layer may consist of a thin layer of a polymer.

If two of the conductors are each provided with a high-resistance layer, covered by the abrasion-resistant layer, the diameter of the overall respective coated conductors can be reduced, because the high-resistance layers can be devised and optimized solely on the basis of their electrical properties, without the need to take mechanical wear into account, due to the protection afforded by the abrasion-resistant coating. Assuming that in conventional leads a polymer coating having a thicknesses exceeding 60 $\mu$m is used, the polymer layer for each conductor in accordance with the invention can be reduced to about 10 $\mu$m to provide sufficient electrical insulation of the conductors from each other.

The abrasion-resistant layer of the coating is preferably a material such as titanium nitride, aluminum oxide or DLC (diamond-like carbon, also known as amorphous diamond), whose abrasion-resistant properties are known. Preferably the abrasion-resistant layer is deposited on the electrically insulating layer in a thickness ranging from 0.1 to 10 $\mu$m, preferably from 1 to 5 $\mu$m.

DESCRIPTION OF THE PREFERRED EMBODIMENTS

Figure 1:
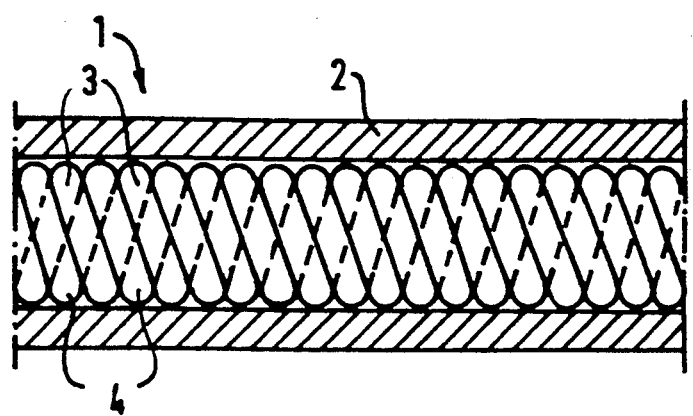
FIG. 1 is a side sectional view of a first embodiment of an electrode lead constructed in accordance with the principles of the present invention.

An electrode lead 1 is shown in FIG. 1 which includes an insulating sheath 2, a first conductor 3 and a second conductor 4. A midsection of the electrode lead is only shown in FIG. 1, it being understood that the lead 1 has a connection contact at one end (not shown) for connecting the electrode lead to a stimulation pulse generator, such as a pacemaker, and at least one electrode tip at the opposite end (not shown) for administering electrotherapy, such as for delivering stimulation pulses from the stimulation pulse generator to surrounding tissue, such as heart tissue.

Figure 2:
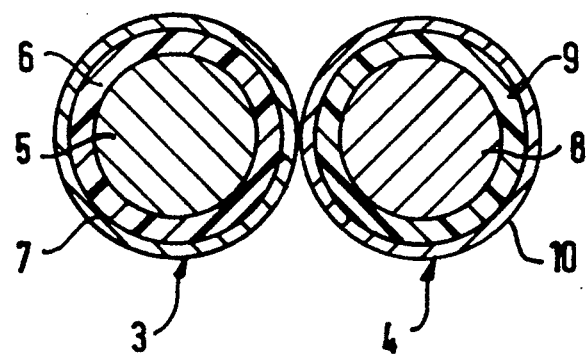
FIG. 2 shows an enlarged cross-section of the two electrode conductors in the electrode lead of FIG. 1.

The first conductor 3 and the second conductor 4 have cross-sections as shown in FIG. 2. The first conductor 3 includes a conductor wire 5, a layer of insulation 6 and an abrasion-resistant coating 7. The second conductor corresponding includes a conductor wire 8, a layer of insulation 9 and an abrasion-resistant coating 10. The function of the abrasion-resistant coatings 7 and 10 is to prevent the underlying insulating coating, which may be a polymer coating, from wearing off of the first conductor 3 and the second conductor 4. The insulation layers 9 and 10 may be polymer coatings of approximately 10 μm in thickness, while the abrasion-resistant coatings 7 and 10 are one or a few microns thick and are made from titanium nitride. In conventional electrode leads having polymer coated conductors, the thickness of the polymer coating exceeds 60 μm. The reduction in the overall diameter of approximately 50 μm may seem modest, but if it is assumed that the conductors 3 and 4 are coiled with an internal diameter, the lead 1 will have an external diameter of approximately 0.7 mm. The reduction in the thickness of the polymer coating means that the overall diameter of the lead 1 can be reduced by about 200 μm, i.e., 0.2 mm, which represents a reduction in diameter by more than 25%.

Figure 3:
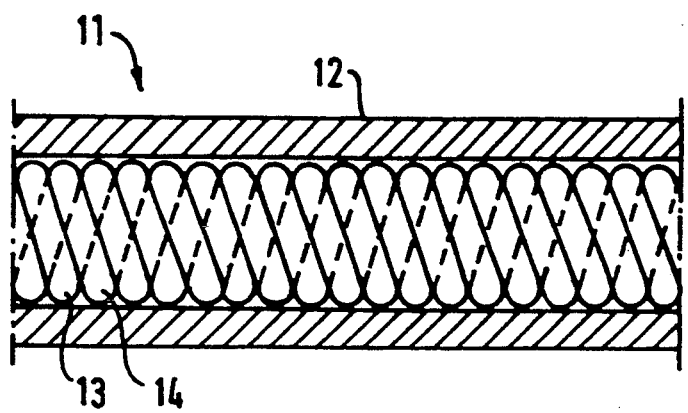
FIG. 3 is a side sectional view of a second embodiment of an electrode lead constructed in accordance with the principles of the present invention.

A further embodiment of an electrode lead 11 is shown in FIG. 3, including an insulating sleeve 12, a first conductor 13 and a second conductor 14. Again, FIG. 3 only illustrates a middle section of the electrode lead 11, which will have a connector contact at one end (not shown) for coupling the electrode lead 11 to a stimulation pulse generator such as a pacemaker, and at least one stimulation electrode at its opposite end (not shown) for delivering electrotherapy such as stimulation pulses from the stimulation pulse generator to surrounding tissue, such as a heart tissue.

Figure 4:
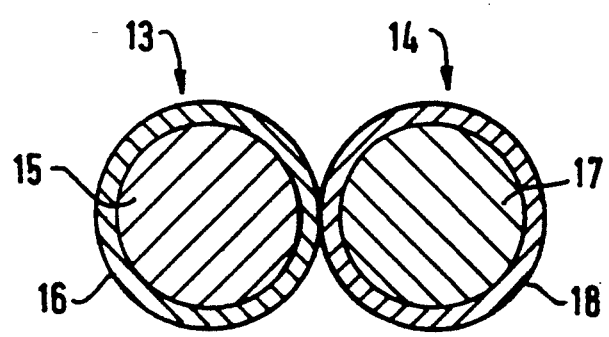
FIG. 4 shows an enlarged cross-section of two electrode conductors in the electrode lead of FIG. 3.

In the embodiment of FIGS. 3 and 4, the first conductor 13 and the second conductor 14 have cross-sections as shown in FIG. 4. The first conductor 13 includes a conductor wire 15 with a high-resistance, abrasion-resistant coating 16. Correspondingly, the second conductor 14 is composed of a conductor wire 17 having a high-resistance, abrasion-resistant coating 18. The purpose of the high-resistance, abrasion-resistant coatings 16 and 18 is to insulate the respective conductor wires 15 and 17 from each other while minimizing the risk of a short circuit arising because of the layers wearing away when the conductors 13 and 14 rub against each other as the electrode 11 is flexed. The high-resistance, abrasion-resistant coatings 16 and 18 are each only a few micrometers thick and made of DLC (diamond-like carbon also known as amorphous diamond).

Although modifications and changes may be suggested by those skilled in the art, it is the intention of the inventors to embody within the patent warranted hereon all changes and modifications as reasonably and properly come within the scope of their contribution to the art.

We claim as our invention:

1. A multipolar electrode lead for a medical apparatus for administering electrotherapy to living tissue, comprising:
    an insulating sheath;
    a first coiled electrical conductor and a second coiled electrical conductor contained in said insulating sheath; and
    at least one of said first and second conductors having a coating directly thereon inside said insulating sheath, said coating completely and individually covering said at least one of said first and second conductors, and said coating being formed by at least one material which is highly-electrically resistant and abrasion-resistant.

2. An electrode lead as claimed in claim 1 wherein said coating is made from amorphous diamond.

3. An electrode lead as claimed in claim 2 wherein said coating comprises a single layer having a thickness in the range of from 0.1 to 10 μm.

4. An electrode lead as claimed in claim 3 wherein said layer has a thickness in the range of from 1 to 5 μm.

5. An electrode lead as claimed in claim 1 wherein said coating comprises a first layer of a highly electrically resistant material and a second layer of an abrasion-resistant material.

6. An electrode lead as claimed in claim 5 wherein said highly electrically resistant material is a polymer.

7. An electrode lead as claimed in claim 5 wherein said abrasion-resistant material is made from a material selected from the group consisting of titanium nitride, aluminum oxide and amorphous diamond.

8. An electrode lead as claimed in claim 5 wherein said layer of abrasion-resistant material has a thickness of from 0.1 to 10 μm.

9. An electrode lead as claimed in claim 8 wherein said layer of abrasion-resistant material has a thickness in the range of from 1 to 5 μm.

10. An electrode lead as claimed in claim 1 wherein said second conductor also has a coating consisting of at least one material which is highly electrically resistant and abrasion-resistant.

11. An electrode lead as claimed in claim 10 wherein said coating is made from amorphous diamond.

12. An electrode lead as claimed in claim 11 wherein said coating comprises a single layer having a thickness in the range of from 0.1 to 10 μm.

13. An electrode lead as claimed in claim 12 wherein said layer has a thickness in the range of from 1 to 5 μm.

14. An electrode lead as claimed in claim 10 wherein said coating comprises a first layer of a highly electrically resistant material and a second layer of an abrasion-resistant material.

15. An electrode lead as claimed in claim 14 wherein said highly electrically resistant material is a polymer.

16. An electrode lead as claimed in claim 14 wherein said abrasion-resistant material is made from a material selected from the group consisting of titanium nitride, aluminum oxide and amorphous diamond.

17. An electrode lead as claimed in claim 14 wherein said layer of abrasion-resistant material has a thickness of from 0.1 to 10 μm.

18. An electrode lead as claimed in claim 17 wherein said layer of abrasion-resistant material has a thickness in the range of from 1 to 5 μm.

* * * * *